United States Patent [19]

Romano et al.

[11] 4,230,881
[45] Oct. 28, 1980

[54] PREPARING OXALIC ACID ESTERS

[75] Inventors: Ugo Romano, Milan; Franco Rivetti, Schio, both of Italy

[73] Assignee: Snamprogetti, S.p.A., Milan, Italy

[21] Appl. No.: 894,139

[22] Filed: Apr. 6, 1978

[30] Foreign Application Priority Data

Apr. 7, 1977 [IT] Italy ............................ 22209 A/77

[51] Int. Cl.³ ...................... C07C 67/36; C07C 69/36
[52] U.S. Cl. .................................. 560/193; 560/204
[58] Field of Search ............................... 560/204, 193

[56] References Cited

U.S. PATENT DOCUMENTS

| | | | |
|---|---|---|---|
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,138,587 | 2/1979 | Yamasaki et al. | 560/204 |

OTHER PUBLICATIONS

March, Advanced Organic Chemistry, 2nd Ed., pp. 285–231 (1977).

*Primary Examiner*—Jane S. Myers
*Attorney, Agent, or Firm*—Morgan, Finnegan, Pine, Foley & Lee

[57] ABSTRACT

A method for the preparation of organic esters of oxalic acid by reaction of carbon monoxide under pressure with the corresponding alcohol is disclosed, the improvement consisting in the use of a quite particular catalyst system. The catalyst is a binary system in which the principal member is a palladium complex and the co-catalyst is a compound, preferably an organic compound having an acidic nature, no matter how weak.

14 Claims, No Drawings

PREPARING OXALIC ACID ESTERS

This invention relates to a method for the preparation of esters of oxalic acid starting from carbon monoxide and an alcohol, in the presence of a catalyst composed of a complex of palladium and a co-catalyst consisting of a substance having acidic properties, according to the following pattern:

$$2\,CO + 2\,ROH \longrightarrow RO-\underset{\underset{O}{\|}}{C}-\underset{\underset{O}{\|}}{C}-OR + H_2 \quad (1)$$

wherein R is an alkyl, aryl, alkaryl, aralkyl or a cycloalkyl group.

The esters of oxalic acid are obtained starting from the free acid according to the conventional esterification methods and find a wide application as synthesis reagents in organic chemistry, especially in the condensation reactions.

The reduction of such esters according to conventional methods leads to the formation of esters of glycolic acid or to ethylene glycol.

More recently, a few patents (U.S. Pat. No. 3,393,136-Germ. Off. No. 2 213 435-Germ. Off. No. 2 514 685-Germ. Off. No. 2 601 139-Japan Kokai 29 428/76-Japan Kokai 157 311/75) have claimed the preparation of such esters starting from carbon monoxide, and alcohol and oxygen, in the presence of appropriate catalysts, with formation of water, according to the pattern:

$$2\,CO + 2\,ROH + \tfrac{1}{2}O_2 \longrightarrow RO-\underset{\underset{O}{\|}}{C}-\underset{\underset{O}{\|}}{C}-OR + H_2O \quad (2)$$

The preparation of the esters in question has also been claimed by means of an electrolytic method with evolution of hydrogen at the cathode, in U.S. Pat. No. 3,393,136.

It has now unexpectedly been found, and this is the subject-matter of this invention, that the preparation of the esters in question can be carried out according to the pattern (1), that is, without employing any oxygen and without any formation of water and without using any electrolytic procedure, but only by adopting an appropriate catalyst system.

The catalyst system of this invention is composed of:
(a) a complex of zerovalent or bivalent palladium.

The complex can also be introduced as such in the reaction system, or it can be generated in situ by means of an appropriate combination of a salt of palladium and a ligand.

By way of example, there are indicated herein, among the palladium complexes (1) complexes of bivalent palladium having the formula
L'L'PdXX', or L"PdXX', wherein L and L' are neutral ligands of the monodentate class among which there are the tertiary amines, the phosphines and the aliphatic and aromatic arsines. L" is a chelating neutral ligand such as an amine, a phosphine or an arsine, all with a chelating character, phenanthroline or dipyridyl or their substituted derivatives, X and X' are anionic ligands such as halides, sulphates, nitrates, carboxylates, alkoxycarbonyls and others.

(2) the complexes of zerovalent palladium of formula $PdL_n'''$ wherein n can be varied from 2 to 4, and L''' is a neutral ligand such as an aliphatic or an aromatic phosphine, or an isonitrile, and the carbonyls of zerovalent palladium of the formula $$Pd_x(CO)_y L_z^{IV}$$

in which x is 1 or 3, y is 1 or 3 and z is 3 or 4 and wherein $L^{IV}$ is a tertiary phosphine.

There are recalled herein still by way of example, as possible combinations of salts and ligands adapted to generate catalytically active species, the combinations of salts of bivalent palladium, such as the nitrate, the acetate and other carboxylates, the halides, the sulphate and others, with the amines and with the tertiary aliphatic and aromatic phosphines and with other neutral ligands of common use.

(b) by a co-catalyst consisting of a substance having acidic properties.

There are indicated herein by way of example, in the list of these substances, the salts of amines such as halohydrides, fluoborates, perchlorates, the organic substances having an even weak acid character due to protons bound to heteroatoms (nitrogen, oxygen), for example the carboxylic acids, the phenols, the imides and sulfimides and others.

The reaction can also be carried out in an inert diluent. There can be used, as diluents organic solvents such as sulphoxides and sulphones (dimethylsulphoxide, tetramethylsulphone), esters (methyl acetate, ethyl acetate, ethylene glycol diacetate), aromatics (benzene, toluene), polyethers (glyme, diglyme), cyclic ethers (tetrahydrofuran, dioxan) and many others.

The reaction can be carried out under carbon monoxide pressures equal to or higher than atmospherical pressure, preferably between 5 and 100 atm., and at temperatures comprised between 30° C. and 300° C., preferably between 50° C. and 200° C.

By way of example and without limitation of the present invention a few examples are reported hereinafter.

EXAMPLE 1

A stainless-steel autoclave is charged with 79 grams of methanol, 1.50 grams of $Pd(OCOCH_3)_2(PPh_3)_2$ and 0.50 grams of succinimide. The autoclave is scavenged with nitrogen and pressurized with carbon monoxide at a pressure of 50 kgs/sq.cm. The autoclave is heated to 120° C. for 10 hours. In the reaction mixture, analyzed for "glc", the presence of dimethyl oxalate (3.2 grams) and of dimethylcarbonate (0.6 grams) has been detected.

EXAMPLE 2

The autoclave is charged with 79 grams of methanol, 1.85 grams pf $Pd(CO)(PPh_3)_3$ and 0.50 grams of succinimide. The autoclave is heated at 120° C. for 10 hours under a pressure of carbon monoxide of 50 kgs/sq.cm. The analysis of the reaction mixture indicates the presence of dimethyl oxalate (2.9 grams) and of dimethyl carbonate (0.5 grams).

EXAMPLE 3

The autoclave is charged with 79 grams of ethanol, 1.85 grams of $Pd(CO)(PPh_3)_3$ and 2.0 grams of formic acid. Heating is effected at 70° C. under a pressure of carbon monoxide of 20 kgs/sq.cm. There are obtained 1.3 grams of diethyl oxalate and 0.2 grams of diethyl carbonate.

EXAMPLE 4

The autoclave is charged with 79 grams of methanol, 2.0 grams of Pd(PPh$_3$)$_4$ and 1.0 gram of diisopropylamine hydrobromide. The autoclave is heated at 120° C. for 4 hours under a pressure of carbon monoxide of 50 kgs/sq.cm.

The "glc" analysis of the mixture after the reaction indicates the formation of dimethyl oxalate (1.7 grams) and dimethyl carbonate (0.3 gram).

EXAMPLE 5

The autoclave is charged with 79 grams of methanol, 1.50 grams of Pd(COOCH$_3$)$_2$(PPh$_3$)$_2$ and 0.70 gram of phthalimide. The autoclave is heated for 4 hours at 150° C. under a pressure of carbon monoxide of 50 kgs/sq.cm. There is obtained 1.1 gram of dimethyl carbonate.

EXAMPLE 6

The autoclave is charged with 79 grams of ethanol, 0.45 gram of palladium acetate, 0.81 grams of tributyl phosphine and 2.50 grams of benzoic acid. The autoclave is heated for 4 hours at 100° C. under a pressure of carbon monoxide of 50 kgs/sq.cm. There are obtained 1.5 gram of diethyl oxalate and 0.2 gram of diethyl carbonate.

EXAMPLE 7

The autoclave is charged with 104 grams of benzyl alcohol, 1.85 grams of Pd(CO)(PPh$_3$)$_3$ and 1.0 gram of triethylamine hydrobromide. The autoclave is heated at 120° C. for 4 hours under a pressure of carbon monoxide of 50 kgs/sq.cm. There are obtained 3.5 grams of dibenzyl oxalate.

EXAMPLE 8

The autoclave is charged with 79 grams of methanol and 1.85 grams of Pd(CO)(PPh$_3$)$_3$. The autoclave is heated at 120° C. for 10 hours under a pressure of 50 kgs/sq.cm. of carbon monoxide. In the reaction mixture, analyzed for "glc" no dimethyl oxalate is detected and not even dimethyl carbonate.

We claim:

1. The method of preparing an ester of oxalic acid from carbon monoxide and an alcohol, wherein the reaction is carried out in the presence of a catalyst consisting of a complex of palladium selected from the group consisting of:
   (a) the complexes of bivalent palladium of the formula LL'PdXX' or L"PdXX' in which L and L' are monodentate neutral ligands, L" is a chelating neutral ligand, X and X', the same or different, are anionic ligands;
   (b) the complexes of zerovalent palladium having the formula PdL'''$_n$ in which n can be varied from 2 to 4, and L''' is a neutral ligand; and
   (c) the complexes of zerovalent palladium of the formula Pd$_x$(CO)$_y$L$^{IV}{}_z$ wherein x is 1 or 3, y is 1 or 3, z is 3 or 4 and L$^{IV}$ is a tertiary phosphine; and
a co-catalyst consisting of a compound having acidic properties selected from the group consisting of amine salts, carboxylic acids, phenol, succinimide and phthalimide.

2. A method as claimed in claim 1, wherein, in the complex of bivalent palladium, L and L' are selected from the group consisting of tertiary amines, phosphines and aliphatic and aromatic arsines, L" is selected from the group consisting of chelating amines, phosphines and arsines, phenanthroline, dipyridly and their substituted derivatives, X and X' are selected from the group consisting of halides, sulphates, nitrates, carboxylates and alkoxy carbonyls.

3. A method as claimed in claim 1, wherein, in the complexes of zerovalent palladium of the formula PdL'''$_n$, L''' is selected from the group consisting of aliphatic and aromatic phosphines and isonitriles.

4. A method as claimed in claim 1, wherein, the reaction is carried out in the presence of an organic solvent selected from the group consisting of sulphoxides, sulphones, esters, polyethers, cyclic ethers and aromatics.

5. A method as claimed in claim 1, wherein, the reaction is carried out under a carbon monoxide pressure at least as high as atmospheric pressure.

6. A method as claimed in claim 1, wherein, the reaction is carried out at a temperature in the range between 30° C. and 300° C.

7. A method as claimed in claim 1, wherein the catalyst is Pd(OCOCH$_3$)(PPh$_3$)$_3$.

8. A method as claimed in claim 1, wherein, the catalyst is Pd(CO)(PPh$_3$)$_3$.

9. A method as claimed in claim 1, wherein the catalyst is Pd(PPh$_3$)$_4$.

10. A method as claimed in claim 1, wherein the co-catalyst is succinimide.

11. A method as claimed in claim 1, wherein the co-catalyst is formic acid.

12. A method as claimed in claim 1, wherein the co-catalyst is benzoic acid.

13. A method as claimed in claim 1, wherein the co-catalyst is diisopropyl amine hydrochloride.

14. A method as claimed in claim 1, wherein the co-catalyst is triethylamine hydrobromide.

* * * * *